United States Patent
Bosley et al.

(10) Patent No.: US 6,737,442 B2
(45) Date of Patent: May 18, 2004

(54) FOOD COMPOSITIONS FOR REDUCING INSULIN RESISTANCE

(75) Inventors: John Anthony Bosley, Sharnbrook (GB); Anna Louise Brown, Sharnbrook (GB); Julia Sarah Rogers, Sharnbrook (GB)

(73) Assignee: Conopco, Inc., Edgewater, NJ (US)

( * ) Notice: Subject to any disclaimer, the term of this patent is extended or adjusted under 35 U.S.C. 154(b) by 0 days.

(21) Appl. No.: 10/152,333

(22) Filed: May 22, 2002

(65) Prior Publication Data

US 2003/0171398 A1 Sep. 11, 2003

(30) Foreign Application Priority Data

May 29, 2001 (EP) .............................. 01304692

(51) Int. Cl.[7] .............................. A61K 31/01
(52) U.S. Cl. .................. 514/762; 514/863; 514/866
(58) Field of Search ................. 514/762, 863, 514/866

(56) References Cited

U.S. PATENT DOCUMENTS

| | | | |
|---|---|---|---|
| 5,612,039 A | 3/1997 | Policappelli et al. | 424/195.1 |
| 5,972,341 A | 10/1999 | Andre et al. | 424/195.1 |

FOREIGN PATENT DOCUMENTS

| | | | |
|---|---|---|---|
| EP | 0 997 149 A1 | 10/1999 | |
| EP | 1 238 590 A1 | 9/2002 | A23D/7/00 |
| JP | 08033464 | 2/1996 | A23L/1/308 |
| WO | WO 98/30199 | 7/1998 | A61K/7/48 |
| WO | WO 01/05356 A1 | 1/2001 | |

OTHER PUBLICATIONS

Al–Awadi et al, "Studies on the Activity of Individual plants on an antidiabetic plant mixture", Acta Diabetologica Latina, 24(1):37–41 (1987).
Subramaniam et al, "Guggul Lipid Reduces Insulin Resistance and Body Weight Gain in C578BI/6 LEP/LEP Mice", International Journal of Obesity, Newman Publishing, London, GB, vol. 25, No. Suppl. 2, S24 (2001).
Kimura, I. et al. New Triterpenes, Myrrhanol A and Myrrhanone A, From Guggul–Gum Resins, and their Potent Anti–Inflammatory Effect on Adjuvant–Induced Air–Pouch Granuloma of Mice (2001) *Biorganic & Medicinal Chemistry Letters 11. 095–989.*
Ubillas, R.P. et al. Antihyperglycemic Furanosesquiterpenes from Commiphora Myrrha. (*1999*) *Planta Med. 65, 778–779.*
Singh, R.B. et al. Hypolipidemic and Antioxidant Effects of Commiphora Mukul as an Adjunct to Dietary Therapy in Patients with Hypercholesterolemia. (1994) *Cardiovascular Drugs and Therapy, 8:659–664.*
Myrrh Absolute (1992) *Food Chem. Toxicol. 30* (*Suppl.*) gis, 918.
XP–002181992, ©Biosis/Biosis ( ) BNSDOCID: xp–002181992.

*Primary Examiner*—Kevin E. Weddington
(74) *Attorney, Agent, or Firm*—Morgan Lewis & Bockius LLP

(57) ABSTRACT

The present invention relates to molecules derived from guggulipid extract which are capable of reducing insulin resistance in humans. The invention further relates food compositions and medicaments comprising such molecules which can be used to treat and/or prevent insulin resistance and the symptoms thereof.

6 Claims, 6 Drawing Sheets

Vehicle       12.5µg/ml Guggul lipid

SEQUENCE LISTING

<160> NUMBER OF SEQ ID NOS: 2

<210> SEQ ID NO 1
<211> LENGTH: 113
<212> TYPE: DNA
<213> ORGANISM: Artificial sequence
<220> FEATURE:
<223> OTHER INFORMATION: Synthetic primer

<400> SEQUENCE: 1

```
gcattcacgc gtcaaatata ggccataggt cattctcgag caaatatagg ccataggtca      60
gattcgatca aatataggcc ataggtcact cgaggcaaca gatcttacgc atg            113
```

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2

```
catgcgtaag atctgttgcc                                                  20
```

FOOD COMPOSITIONS FOR REDUCING INSULIN RESISTANCE

FIELD OF THE INVENTION

The invention relates to the field of natural plant derived ingredients which have beneficial properties to health. More particularly the invention relates to ingredients derived from the Indian plant *Commiphora mukul* and their novel use in addressing the human condition of insulin resistance and health problems associated therewith.

BACKGROUND OF THE INVENTION

Insulin is a hormone well known to play a key role in maintaining blood glucose levels within healthy parameters. Where the action of insulin is impaired, as is the case in the human condition insulin resistance, a range of health problems can occur. In the short term the health problems associated with insulin resistance comprise chronic fatigue, cognitive impairment and mood swings, whilst long term they include more chronic diseases such as cardiovascular disease, type-II diabetes and polycystic ovary syndrome. Insulin resistance is therefore a complex metabolic condition and the frequency of incidence within the human population makes it highly desirable to develop a means by which it can be controlled or prevented.

PPARgamma is a known member of the peroxisome proliferator activated receptor (PPAR) subset of the nuclear hormone receptor superfamily. It is a ligand activated transcription factor and binds DNA in a heterodimeric complex with a second nuclear hormone receptor RXR. PPARgamma has been characterised as an important regulator of lipid metabolism. PPARgamma is suggested as playing a role in insulin sensitivity and other biological activities including effects on inflammation, cancer, cognition and cellular differentiation.

*Commiphora mukul* has long been used as a herbal treatment for hyperlipidaemia in the form of a gum resin called "guggulipid" or "guggal lipid", however little is known in the art about the effect of this plant at a molecular level. EP 0997149 discloses that the pharmacological activity of guggulipid is attributable to known ketonic steroids the E- and Z-guggulsterones, however contrary to expectation, the pharmacological activity of guggulipid with respect to PPARgamma receptor activity has been found by the applicants not to be attributable to these guggulsterones.

Guggulipid has been disclosed as an agent for the treatment of autoimmune diseases by virtue of its anti-inflammatory effect. In this context the autoimmune form of diabetes i.e. type-1 has been noted. Guggulipid has also been included in compositions for dietary supplementation (EP997149).

Insulin resistance is a causative agent of type-2 diabetes and is distinct from the autoimmune type-1 form. At the time of filing the influence of guggulipid on human insulin resistance and in particular the influence of guggulipid on PPARgamma receptors was not known.

The objective technical problem to be solved by the present invention is to provide food compositions comprising naturally derived ingredients which are capable of inducing human health benefits by the treatment and/or prevention of insulin resistance. In particular the invention addresses the problem of providing natural ingredients which are capable of treating or preventing insulin resistance by activating PPARgamma receptors.

The applicants have found that compounds present in the natural plant extract guggulipid offer a novel solution to the defined problem, thereby providing naturally derived ingredients capable of treating and/or preventing insulin resistance via PPARgamma receptor activation.

The prior art is silent as to any suggestion that a guggulipid extract may have PPARgamma activating properties and the applicants are aware of no connection having been established in the art between guggulipid or its components and insulin sensitivity.

BRIEF DESCRIPTION OF THE INVENTION

The problem of providing food compositions which treat and/or prevent insulin resistance in humans has now been solved by providing in a first object of the invention, a food composition for the treatment and/or prevention of insulin resistance in humans comprising an effective amount of a compound according to the formula;

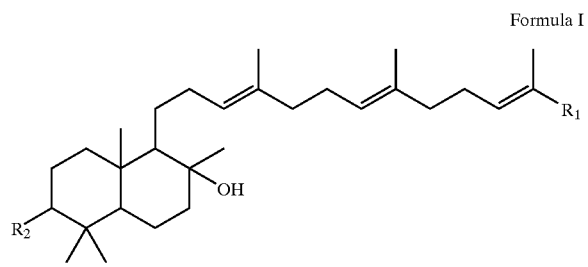

Formula I wherein, $R_1$ is selected from the group consisting of COOH, $CH_2OH$ including salts and/or esters thereof and $CH_3$; and $R_2$ is selected from the group consisting of OH, O and esters thereof;

wherein said compound is contained within continuous or discontinuous fat phase.

It is a second object of the invention to provide a food composition for the treatment and/or prevention of insulin resistance in humans comprising an effective amount of a compound according to the formula described above wherein said compound is contained within a continuous or discontinuous aqueous phase.

A preferred embodiment comprises a food composition as described above wherein said compound is present in an amount of at least 0.01% by weight.

It is a third object of the invention to provide a food composition for the treatment and/or prevention of insulin resistance in humans wherein said composition comprises a compound as described above in an amount of at least 3% by weight.

In a fourth object the present invention provides food composition according as described above for use in the treatment and/or prevention of diseases selected from the group comprising polycystic ovary syndrome, type-2 diabetes, gestational diabetes, syndrome X, hypertension, psoriasis and stroke.

A fifth object of the invention provides a food composition according to any one of claims 1 to 4 for use in the treatment and/or prevention of one or more symptoms of insulin resistance selected from the group comprising reduced energy levels, reduced cognitive performance, tiredness and mood swings.

In a preferred embodiment the food composition of the invention is preferably, selected from the group comprising edible spreads, mayonnaise, dressing, ice cream, dairy and non-dairy creams, confections, bakery products, soups, beverages, jam, cakes, chocolate, dietary supplements, sauces and speciality foods for type-2 diabetics.

Conventional fractions of the commercially available guggulipid extract which have been processed for food compositions have an undesirable bitterness and accordingly are unpleasant to taste. In contrast neither compounds identified by the invention nor fractions of the guggulipid extract which have been enriched for these compounds have the bitterness associated with conventional fractions of the guggulipid extract.

Particular advantage is therefore offered by incorporating either the compounds according to formula I or a fraction of guggulipid extract enriched for such compounds into a food composition. In this way the favourable health benefits are maintained with no flavour detriment.

A sixth object of the invention therefore provides for the use of a fraction of a guggulipid extract in the manufacture of a food composition for the treatment and/or prevention of insulin resistance wherein said fraction comprises at least 15 wt % of a compound according to claim 1 and less than 1.0 wt % of Z and E guggulsterones;

It has also been found that crude guggulipid extract may induce dehydration, however, these effects can be avoided by applying the novel guggulipid fractions of the guggulipid extract provided herein which are enriched for one or more compounds according to formula I in place of the crude guggulipid extract.

It is therefore a seventh object of the invention to provide a blend of a guggulipid fraction and another component wherein said blend comprises;

(i) a guggulipid fraction comprising more than 15 wt %, compound according to formula I, and;

(ii) tri and/or diglycerides including fatty acids and their esters, in such amounts that the blend contains at least 2 wt % of the guggulipid fraction.

Preferably the guggulipid fraction used in the manufacture of a food composition and in the blend will comprise more than 20 wt %, more preferably more that 40 wt %, most preferably more than 60 wt % of a compound according to the formula I.

In a most preferred embodiment the invention comprises a blend as described above wherein the compound according to formula I is 13-(decahydro-2-hydroxy-2,5,5,8a-tetramethyl-6-oxo-1-naphthalenyl)-2,6,10-trimethyl-tridecatrienoic acid.

Conjugated linoleic acid (CLA) is known in the art for use in body weight management, however it has been found that under certain circumstances this may have the effect of reducing insulin sensitivity in some humans. This effect can be countered by combination of CLA in a blend with an effective amount of a guggulipid fraction according to the invention or compound according to formula I.

A further preferred embodiment of the invention therefore comprises a blend comprising a guggulipid fraction and another component wherein the guggulipid fraction is the fraction as described above and the other component is a compound with at least 40 wt % CLA in it, whereby the CLA can be present as free fatty acid, as tri-or partial glyceride or as alkyl ester of CLA and whereby the blend contains at least 20 wt % CLA residues.

The application of a crude guggulipid extract for the treatment and/or prevention of insulin resistance suffers the disadvantage that the crude extract may cause dehydration in some consumers. Through the application of guggulipid fractions identified herein the invention provides a method for treating and/or preventing insulin resistance either inherent to the consumer or associated with CLA consumption, wherein said consumer is administered an effective amount of a guggulipid fraction described above, or a blend as described above.

An embodiment of the invention is also directed to food compositions comprising a blend as described above.

An eighth object of the invention provides a compound according to formula I for use as a medicament.

Via activation of a PPARgamma receptor a compound according to formula I has a positive effect of reducing insulin resistance. The invention therefore preferably embodies either guggulipid extract or a compound according to according to formula I for use in the treatment and/or prevention of insulin resistance in humans.

Insulin resistance has a large number of associated disorders in humans and as a result a compound according to formula I has widespread health benefits. In a further preferred embodiment the invention is therefore directed to a compound according to formula I for use in the treatment and/or prevention of one or more diseases selected from the group comprising polycystic ovary syndrome, type-2 diabetes, gestational diabetes, syndrome X, hypertension, psoriasis and stroke.

Since insulin resistance is a key cause of diabetes type-2 a preferred embodiment of the invention relates to a use as described above for the treatment and/or prevention of type-2 diabetes.

The associated disorders of insulin resistance have a number of common symptoms, therefore in a further preferred embodiment the invention is directed to a compound according to formula I for use in the treatment and/or prevention of one or more symptoms of insulin resistance selected from the group comprising reduced energy levels, reduced cognitive performance, tiredness, spatial disorientation, clinical depression and mood swings.

An ninth object of the invention provides a compound according to formula 1 for use in the manufacture of a composition, preferably a food composition, for the treatment and/or prevention of insulin resistance in humans.

Preferably the invention embodies a compound according to formula I for use in the manufacture of a composition for the treatment and/or prevention of one or more diseases selected from the group comprising polycystic ovary syndrome, type-2 diabetes, gestational diabetes, syndrome X, hypertension, psoriasis and stroke.

A further preferred embodiment relates to a compound according to formula I for use in the manufacture of a composition for the treatment and/or prevention of one or more symptoms of insulin resistance selected from the group comprising reduced energy levels, reduced cognitive performance, tiredness, spatial disorientation and clinical depression.

Detailed description of the invention

Guggulipid extract is used herein to refer to a solvent extract of guggulipid gum resin, however it is recognised that other starting materials derived from the *Commiphora mukul* plant may be used. Extraction from the gum resin may be performed with any suitable solvent, however it is preferable that ethyl acetate is used as this has been found to be a particularly effective solvent. A suitable guggulipid extract is commercially available from Indena as Gukkaselect™.

In a compound according to formula I where $R_1$ is COOH, an ester thereof will preferably comprise a linear or branched, substituted or unsubstituted alkyl group containing from 1 to 32 carbon atoms. Most preferred where $R_1$ is COOH, esters thereof preferably contain an alcohol group containing from 1 to 12 carbon atoms (including C1,C2,C3, C4,C5,C6,C7,C8,C9,C10,C11 and C12 alcohol groups).

Where $R_1$ or $R_2$ comprises an OH group esters thereof preferably comprise an acid group containing from 1 to 22 carbon atoms, most preferred from 6 to 18 carbon atoms (including C6,C7,C8,C9,C10,C11,C12,C13,C14,C15,C16, C17 and C18 acid groups.)

Preferably when $R_1$ is COOH, $R_2$ is O and most preferably the compound is in the form of a 13-(decahydro-2-hydroxy-2,5,5,8a-tetramethyl-6-oxo-1-napthalenyl)-2,6,10-trimethyl-2,6,10-Tridecatrienoic acid for example 13-(decahydro-2-hydroxy-2,5,5,8a-tetramethyl-6-oxo-1-napthalenyl)-2,6,10-trimethyl-[1R-[1α(2E,6E,10E)2β,4β, 8aα]]-2,6,10-Tridecatrienoic acid (9Cl) also known as commipherin or commipheric acid.

Preferably when $R_1$ is $CH_2OH$, $R_2$ is O or OH. Most preferably $R_2$ is O and the compound is in the form of a octahydro-6-hydroxy-5-(13-hydroxy-4,8,12-trimethyl-3,7, 11-tridecatrienyl)1,1,4a,6-tetramethyl-2(1H)-naphthalenone, for example octahydro-6-hydroxy-5-(13-hydroxy-4,8,12-trimethyl-3,7,11-tridecatrienyl)-1,1,4a,6-tetramethyl-[4aS-[4aα,5α(3E,7E,11E),6β,8aβ]]-2(1H)-naphthalenone also known as commipherol.

Preferably when $R_1$ is $CH_3$, $R_2$ is OH and the compound is preferably decahydro-1,1,4a,6-tetramethyl-5-[(3E,7E)-4, 8,12-trimethyl-3,7,11-tridecatrienyl]-,(4aS,5R,6R,8aR)-2,6-Naphthalenediol.

It has been found that commipheric acid is particularly effective in reducing insulin resistance in humans therefore in a most preferred embodiment the compound according to formula I is commipheric acid.

It is appreciated that a plurality of compounds according to the above defined formula may be suitably incorporated into a composition of the invention to provide an effective amount thereof. Accordingly the singular usage of 'a' compound in this description is taken to encompass such a plurality of compounds in combination within a composition of the invention.

Where a food composition according to present invention comprises a compound according to formula I within a fat phase thereof, this fat phase may be continuous or discontinuous. In certain products such as a margarine, the compound is suitably provided in the continuous fat phase therein. For a continuous fat phase system a food composition of the present invention preferably comprises at least 5 wt % fat, preferably less than 90 wt % fat, more preferably the fat component of the composition comprises from 20 to 80 wt % fat, most preferably from 30 to 50 wt % fat.

In alternative systems such as those found in sauces, soups, dressings, meal replacement bars, mayonnaise, dairy/non-dairy cream or ice cream etc. the compound of formula I is more likely to be present in a discontinuous fat phase, either as an oil in water emulsion or within discrete solid fat droplets.

Oil in water emulsions in accordance with the present invention preferably use emulsifiers with HLB values in the range 8 to 18 and/or polymeric stabilisers. The person skilled in the art will be aware of emulsifiers that fall within this HLB range. Suitable food grade emulsifiers and stabilisers used for preparation of oil in water emulsions may be selected from one or more of the group comprising lecithins (phospholipids), sodium caseinate, gum arabic, deacetylated tartaric esters of monoglycerides (DATEM), sucrose esters of fatty acids, polyglycerol esters of fatty acids (PGE), polysorbate 60, polysorbate 65 and polysorbate 80.

The amount of emulsifier and/or stabiliser used in a oil in water composition will depend on the droplet size, the relative phase volumes and stability of emulsion required. Typically the amount will range from 1 to 10 wt %, but may for particular examples range from 0.5 to 30 wt %.

The fat content of a product with a discontinuous fat phase can vary widely depending on the nature of the product. A product such as mayonnaise will typically contain around 85 wt % fat whereas a sauce such as tomato sauce may contain 0.1 wt % fat. Preferably products with a discontinuous fat phase comprise at least 0.1 wt % fat, preferably less than 90 wt % fat, more preferably the fat component of the composition comprises from 5 to 50 wt % fat, most preferably from 10 to 20 wt % fat.

A meal substitute such as a meal replacement bar will suitably comprise a compound as described above wherein said compound is provided within a discontinuous oil phase.

Compounds according to the formula I are poorly soluble in aqueous conditions, hence dispersal of the compound in an aqueous phase has been found to be most effectively achieved through the use of one or more carrier molecules. Such carrier molecules are preferably food grade emulsifiers with HLB values in the range 8 to 18, more preferably one or more selected from the group comprising comprising lecithins (phospholipids), sodium caseinate, gum arabic, deacetylated tartaric esters of monoglycerides (DATEM), sucrose esters of fatty acids, polyglycerol esters of fatty acids (PGE), polysorbate 60, polysorbate 65 and polysorbate 80

Oil in water emulsion compositions according to the present invention may suitably be spray dried by conventional techniques known to the person skilled in the art to give powder supplements which may be added to other food compositions, in particular beverages. Powdered sodium caseinate oil in water emulsions are preferably provided in powdered form.

Powders have been produced by a process wherein Dynasan 118 (Stearic acid triglyceride, SASOL) containing 10 wt % of guggul or enriched commipheric acid was melted at 90° C. with stirring. The material was then cooled quickly to −18° C., placed in a blender with some pellets of dry ice, and ground into a fine powder.

The provision of such aqueous based systems allows the compounds of interest to suitably incorporated into low or non-fat containing products such as beverages, meal replacement drinks, soups and sauces.

The determination of an effective amount of the compound according to formula I within a food composition according to the present invention will depend on the amount of the food composition that is to be consumed within a daily period. Individual human consumption of one or more food compositions according to the invention should comprise sufficient compound to provide a average daily dosage of from 0.1 to 5 grams. Preferably daily consumption ranges from 0.5 to 2 grams, most preferred 1.0 to 1.5 grams to achieve the desired effect on insulin resistance.

The present invention provides novel food compositions wherein an effective compound as described above is provided in an aqueous or a fat phase. Preferably an effective amount is greater than 0.01 wt % of the consumed food composition, more preferably less than 20 wt %, most preferred between 0.1 wt % and 5 wt %.

The amount of daily consumption of a spread type product such as a margarine is comparatively low hence the extent of supplementation is preferably quite high. Such products may be suitably supplemented with a compound as defined above to at least 0.3 wt %, preferably less than 20 wt %, more preferred from 0.5 to 10 wt %. In a most preferred embodiment such products comprise a compound as defined above in an amount from 1 to 5 wt %.

In contrast the amount of daily consumption of beverage may be considerably higher than that of a spread and hence in such an embodiment of the invention is suitably supplemented with a compound as defined above to at least 0.01 wt % of the beverage as consumed. Dilutable concentrates would be supplemented to a level which achieves at least 0.01 wt % of the beverage when diluted for consumption. Preferably the supplementation of a beverage according to the invention is less than 0.5 wt % of the beverage as consumed, most preferably supplementation is within the range from 0.05 to 0.2 wt %. Ready to drink tea may suitably be supplemented in accordance with this regime.

Food compositions such as soups preferably comprise a compound as described above in an amount from 0.01 to 2.5 g per serving. Typically such compositions will comprise at least 0.03 wt % of said compound, preferably less than 2 wt %, more preferred from 0.1 to 1 wt %, most preferred from 0.25 to 0.5 wt %.

Where the food composition is a meal replacement bar or meal replacement drink, this is ideally supplemented with an amount of compound according to the above description of at least 0.03 and less than 1.6 grams per bar or drink, preferably from 0.1 to 1.0 grams, most preferred from 0.25 to 0.5 grams per bar or drink.

Through the consumption of one or more of the food compositions according to the invention the consumer may ensure that a dosage of from 0.1 to 5 grams of compound is ingested. By combining different food compositions as disclosed herein the consumer can gain a varied diet while ensuring the treatment and/or prevention of insulin resistance. An embodiment of the invention therefore comprises a combination of food compositions as described above for the treatment and/or prevention of insulin resistance in humans, wherein said combination is dictated by a predetermined diet plan.

The present invention also provides a novel food composition for the treatment and/or prevention of insulin resistance in humans wherein said composition comprises at least 3 wt % of a compound according to the above description. Compositions known in the art which contain crude guggulipid extract do not provide such levels of the active compounds identified herein and so do not have the ability as provided herein to influence insulin sensitivity. Preferably food compositions which comprise at least 3 wt % of a compound according to the above description are provided in the form of nutritional supplements such as capsules, tablets or powders.

Identifying those compound within guggulipid extract which activate PPARgamma involved the strategy illustrated in FIG. 1. Fractionation of the guggulipid extract is preferably performed initially by silica gel column fractionation with any subsequent sub-fractionation being preferably conducted by HPLC. Fractions and sub-fractions are analysed using a reporter gene assay to determine which has been enriched for molecules capable of activating PPARgamma. Additional cycles of the sub-fractionation process may be performed until no further enrichment for PPARgamma activating molecules can be detected. The final sub-fractions may then be characterised using structural techniques e.g. GCMS analysis.

PPARgamma receptor activity is determined by a suitable reporter gene assay. Preferably the reporter gene assay used comprises the transcription induction of a luciferase gene. Levels of firefly luciferase (normalised against the renilla luciferase control) provide a measure of reporter gene activity which in turn reflects the level of activation.

In a preferred embodiment the invention therefore provides a process for identifying compounds capable of activating a PPARgamma receptor wherein said process comprises the steps;
(i) fractionating a guggulipid extract;
(ii) selecting a fraction with PPARgamma receptor activity;
(iii) optionally repeating steps (i) and (ii) until no further increase in PPARgamma receptor activity in said fraction is observed;

CLA is known to display a number of health benefits such as weight control, fat control, muscle mass, etc but we have also found that sometimes CLA may also have a negative impact on insulin resistance. Intake of the guggulipid extract may alleviate these negative effects, but give rise to the further effect of dehydration. Fractions of the extract provided by the above process and most particularly the compounds according to formula I are able to alleviate the insulin resistance effect of CLA without giving rise to dehydration.

On the basis of the finding by the applicants that gugglipid extract comprises molecules which can activate PPARgamma receptors, this receptor activation and the associated reporter gene assay has been shown to be an effective means of screening fractions of the guggulipid extract. Fractionation and sub-fractionation of those samples screening positive for activity, has thereby made it possible to provide compositions with improved receptor binding activity over the commercially available guggulipid extract. These compositions are thus far more effective at increasing insulin sensitivity in a patient than the commercially available guggulipid extract.

Intermediate fractions which have undergone at least one fractionation and show enhanced activity over the guggulipid extract are referred to herein as enriched guggulipid extract or guggulipid fractions.

Optimisation for PPARgamma activity has the additional advantage that it removes undesirable components from the guggulipid extract. In particular it has been found that the repeated fractionation and sub-fractionation gives rise to a significant reduction in the undesirable bitter taste associated with the crude guggulipid extract form. This bitterness may be reduced further by the requirement to use less as a result of increased activity in enriched fractions.

Such improvement in flavour and enhanced activity makes the enriched guggulipid extract highly advantageous for many orally consumed compositions. Accordingly enriched guggulipid extract may be used in the treatment and/or prevention of insulin resistance in a similar manner to those compounds identified herein as the active molecules which are obtainable therefrom.

EXAMPLE 1

Silica Gel Column Fractionation

The staring material is an ethyl acetate extract of guggulipid 'gukkaselect' obtained from Indena. Guggulipid extract is dissolved in ethyl acetate and separated using a silica gel column (10 g guggulipid through 100 g silica gel). The solvents used for elution are detailed in table 1, volumes of 250 mL are used in each case

TABLE 1

| Fraction | Solvent (250 mL) |
| --- | --- |
| 1 | Hexane |
| 2 | Hexane/ethyl acetate 95/5 |
| 3 | Hexane/ethyl acetate 90/10 |
| 4 | Hexane/ethyl acetate 80/20 |
| 5 | Hexane/ethyl acetate 60/40 |
| 6 | Hexane/ethyl acetate 50/50 |
| 7 | Hexane/ethyl acetate 40/60 |
| 8 | Hexane/ethyl acetate 30/70 |
| 9 | Hexane/ethyl acetate 20/80 |
| 10 | Hexane/ethyl acetate 10/90 |
| 11 | Hexane/ethyl acetate 5/95 |
| 12 | Ethyl acetate |
| 13 | Ethyl acetate/methanol 8020 |
| 14 | Ethyl acetate/methanol 60/40 |
| 15 | Ethyl acetate/methanol 40/60 |
| 16 | Ethyl acetate/methanol 20/80 |
| 17 | Methanol |

Figure 4:
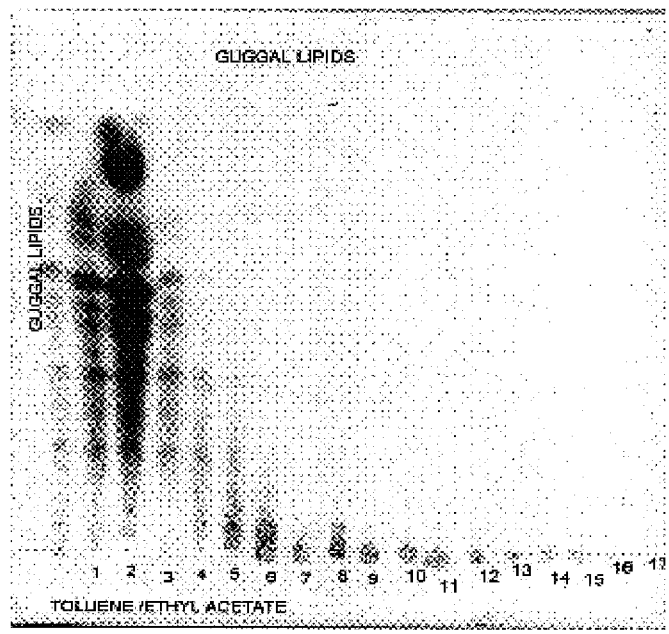
FIG. 4: illustrates a thin layer chromatography plate for silica gel fractions of guggulipid extract eluted with toluene/ethyl acetate.

FIG. 4 provides a thin layer chromatography plate for silica gel fraction of guggulipid extract with toluene/ethyl acetate.

Reporter Gene Assay

This assay is based on that described by Kliewer et al (Nature 358 771–774 1992). In brief, cos-7 cells (ECACC No. 87021302) were seeded in 24-well plates at a density of $0.325 \times 10^5$ cells/well. Cells were grown overnight at 37° C./5% $CO_2$ in DMEM containing 10% FCS, 2 mM L-glutamine, 100 iu/ml penicillin and 100 g/ml streptomycin. Cells were washed with transfection media (DMEM containing 2 mM L-glutamine) then transiently transfected with 4 plasmids: a PPAR-responsive firefly luciferase reporter gene (pPPRE3TK-luc); mammalian expression plasmids (pcDNA3/hPPARγ1 and pRSV/hRXRα) containing human PPARγ1 and RXRα cDNAs respectively and a control plasmid (pRLTK, Promega) which constitutatively expresses the renilla luciferase gene. Transfection was performed using Lipofectamine (Gibco Brl) as directed by the manufacturers. Transfected cells were incubated for 6 h at 37° C./5% $CO_2$ and then for a further 46 hours in the presence or absence of ligand. After 46 hours cell lysates were prepared and the level of firefly and renilla luciferase determined using the Dual luciferase assay system (Promega) and a MLX microtitre plate luminometer (Dynex). The level of firefly luciferase (normalised against the renilla luciferase control) provides a measure of reporter gene activity. This in turn reflects,the level of PPARγ activation.

Preparation of pPPRE3TK-luc

A double-stranded PPAR-binding site was prepared using the 'Klenow fill-in' technique. A 113 bp oligonucleotide (PPRE1/3) containing a triplet of PPREs and appropriate restriction endonuclease sites was designed. PPRE1/3 and a 20 bp oligonucleotide (PPRE1/3R) complementary to the 3' region of PPRE1/3 were synthesised.

PPRE1/3 (SEQ ID NO. 1)

5'-GCATTCACGCGTCAAATATAGGCCATAGGTCAT
TCTCGAGCAAATATAGGCCATAGGTCAGATT
CGATCAAATATAGGCCATAGGTCACTCGAGGC
AACAGATCTTACGCATG-3'

PPRE1/3R (SEQ ID NO. 2)

5'-CATGCGTAAGATCTGTTGCC-3'

In a final volume of 20 µl 2 µg of PPRE1/3R was annealed to 2 µg of PPRE1/3 by boiling for 5 minutes and then cooling slowly to room temperature. Annealed PPRE1/3R was used to prime second-strand DNA synthesis. A 30 µl reaction mix containing 20 µl annealed DNA, 1.5 µl 2 mM dNTPs, 1× Klenow Buffer and 5 units DNA Polymerase I (Klenow fragment) was incubated for 1 hour at 37° C. and then 10 minutes at 75° C. A 5 µl sample of the synthesised product was analysed on a 3% agarose gel. The remaining product was purified by ethanol precipitation and resuspended in sterile water. The double-stranded PPAR-binding site (insert) was digested with MluI and BglII for 1 hour at 37° C. and then purified by ethanol precipitation. 1 µg of the vector pNF-κB-luc (Clontech) was digested with MluI and BglII for 1 hour at 37° C. and then analysed on a 1% agarose gel. Digested DNA was purified from the gel using a Qiaquick Gel Extraction Kit (Qiagen). Digested vector and insert DNA were incubated for 4 hours at room temperature in a volume of 15 µl containing 1× ligase buffer and 5 units T4 DNA ligase. The full ligation reaction was used to transform competant E.coli JM109 cells (Promega).

TABLE 2

Effect of guggulipid extract on activation of PPARγ:

| Guggulipid extract | Reporter gene activity (Fold-induction relative to the vehicle) | |
| --- | --- | --- |
| (µg/ml) | Mean | St err |
| Vehicle | 1.0 | 0.06 |
| 0.5 | 1.4 | 0.05 |
| 1.25 | 1.9 | 0.11 |
| 2.5 | 2.6 | 0.25 |
| 3.75 | 4.0 | 0.51 |
| 5 | 5.5 | 0.52 |

The presence of guggulipid stimulates reporter gene activity in a dose-dependent manner. Reporter gene expression is controlled by PPARgamma and therefore reflects the level of PPARgamma activation. Hence these data show that guggulipid is acting as an activator of PPARgamma.

TABLE 3

Effect of guggulipid fractions generated by silica gel chromatography on reporter gene activity.

| Guggulipid fraction (2.5 μg/ml) | Reporter gene activity* (Fold-induction relative to vehicle) | |
|---|---|---|
| | Mean | St Err |
| Vehicle | 1.0 | 0.02 |
| Gukkaselect | 5.0 | 0.20 |
| Fraction 1 | 1.7 | 1.15 |
| Fraction 2 | 1.2 | 0.15 |
| Fraction 3 | 1.8 | 0.72 |
| Fraction 4 | 4.1 | 0.77 |
| Fraction 5 | 8.0 | 0.6 |
| Fraction 6 | 4.1 | 0.29 |
| Fraction 7 | 1.8 | 0.51 |
| Fraction 8 | 1.2 | 0.40 |
| Fraction 9 | 1.2 | 0.2 |
| Fraction 10 | 0.5 | 0.19 |
| Fraction 11 | 1.0 | 0.38 |
| Fraction 12 | 0.9 | 0.25 |
| Fraction 13 | 1.2 | 0.13 |
| Fraction 14 | 1.2 | 0.33 |
| Fraction 15 | 3.7 | 1.12 |
| Fraction 16 | 6.1 | 0.4 |
| Fraction 17 | 5.9 | 0.26 |

*Reporter gene expression is controlled by PPARγ and therefore reflects the level of PPARγ activation Analysis of the silica gel column generated fractions of guggulipid shows that molecules capable of activating PPARgamma are enriched in fractions 5, 16 and 17.

HPLC Fractionation

Fractions enriched for molecules capable of activating PPARgamma were sub-fractionated using a normal-phase HPLC system.

HPLC System

Silica column—150×4.6 mm packed with Nucleosil 100-3 (3 um) silica with a guard column (silica cartridge, 4 mm×3 mm id).

Solvent system: Solvent A—isohexane HPLC

Solvent B—Methanol 75: tetrahydrofuran 25 v/v+0.01%v trifluoroacetic acid

TABLE 4

Gradient (i):

| Time mins | % A | % B |
|---|---|---|
| 0 | 97 | 3 |
| 5 | 97 | 3 |
| 15 | 88 | 12 |
| 25 | 80 | 20 |
| 30 | 80 | 20 |
| 35 | 97 | 3 |
| 45 | 97 | 3 |

Flow-rate 1.0 mL/min. Detector—model 950/14 ELSD (Polymer Labs). Nitrogen 10 L/min, temperature 40C. Electronic switching-valve on column outlet to allow collection of selected fractions on a time-basis.

TABLE 5

Effect of guggulipid subfractions generated by the HPLC separation of fraction 5 on reporter gene activity

| Guggulipid (1.25 μg/ml) | Reporter gene activity* (Fold-induction relative to vehicle) | |
|---|---|---|
| | Mean | St Err |
| Vehicle | 1.0 | 0.35 |
| Fraction 5 | 4.08 | 0.06 |
| Subfraction 1 | 1.6 | 0.7 |
| Subfraction 2 | 1.3 | 0.28 |
| Subfraction 3 | 3.0 | 0.48 |
| Subfraction 4 | 5.3 | 0.89 |
| Subfraction 5 | 0.7 | 0.11 |

Figure 5:
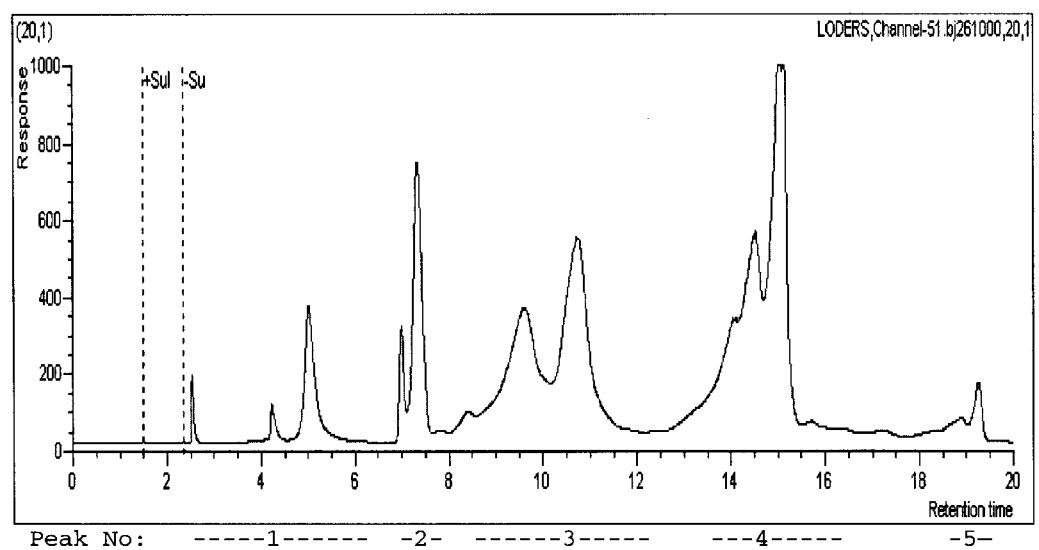
FIG. 5: shows a HPLC trace wherein molecules activating PPARgamma are further enriched in sub-fraction 4.
Figure 6:
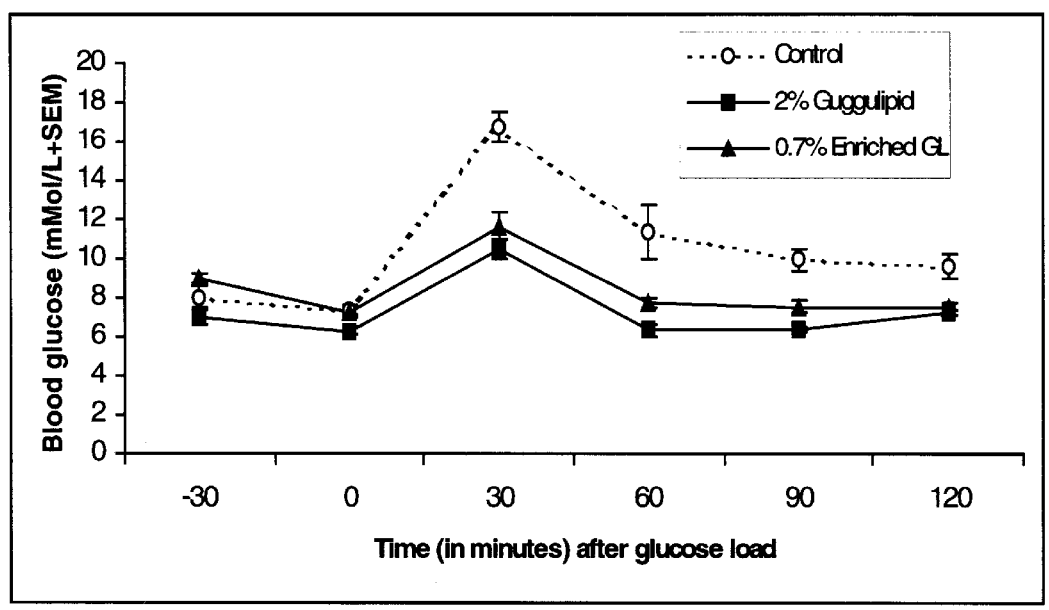
FIG. 6: illustrates that commipheric acid is the component of the guggulipid extract which improves glucose tolerance, a guggulipid fraction enriched for commipheric acid provides beneficial effects at lower concentration than standard guggulipid extract.

*Reporter gene expression is controlled by PPARgamma and therefore reflects the level of PPARgamma activation Analysis of HPLC generated subfractions of fraction 5 shows that the molecules activating PPARgamma are further enriched in sub-fraction 4 (FIG. 5)

TABLE 6

This analysis was repeated with the following gradients:

| Time mins | % A | % B |
|---|---|---|
| 0 | 97 | 3 |
| 5 | 97 | 3 |
| 20 | 88 | 12 |
| 25 | 97 | 3 |
| 30 | 97 | 3 |

Flow-rate 1.0 mL/min. Detector—model 950/14 ELSD (Polymer Labs). Nitrogen 10 L/min, temperature 40° C. Electronic switching-valve on column outlet to allow collection of selected fractions on a time-basis.

| Peak collection windows: | |
|---|---|
| 6–10 minutes | fraction A |
| 10–14 minutes | fraction B |
| 14–18 minutes | fraction C |
| 18–21 minutes | fraction D |

TABLE 7

Effect of guggulipid subfractions generated by the HPLC separation of fraction 5 on reporter gene activity

| Guggulipid extract (1.25 μg/ml) | Reporter gene activity* (Fold-induction relative to vehicle) | |
|---|---|---|
| | Mean | St Err |
| Vehicle | 1 | 0.15 |
| Fraction A | 1.32 | 0.26 |
| Fraction B | 5.1 | 0.5 |
| Fraction C | 1.02 | 0.13 |
| Fraction D | 1.05 | 0.06 |

*Reporter gene expression is controlled by PPARgamma and therefore reflects the level of PPARgamma activation Analysis of the sub-fractions A–D isolated by HPLC separation of silica column generated guggulipid fraction 5 shows that the molecules which activate PPARgamma appear to be present in fraction B.

Analysis of Fraction 5

The acidic components from guggul lipid were isolated by SPE using Varian Mega Bond Elut (2 g) aminopropyl columns.

A 2 g aminiopropyl SPE column (Varian mega bond elut) was placed on a vacuum manifold and washed twice with 8 mL of hexane. Approx. 200 mg (weight accurately recorded) guggul lipid (gukkaselect, ex Indena, Milan) was dissolved in 2.0 mL chloroform and applied to the column under gravity. The column was eluted with 18 mL chloroform/2-propanol (2:1) to recover neutral lipids. The column was then eluted with 18 mL 2% acetic acid in diethyl ether to recover the acidic components.

The solvent was removed from the recovered fractions under nitrogen on a hot block set at 80° C.

GC-MS Analysis

For GC-MS characterisation, the acidic components isolated by aminopropyl column chromatography were reacted with 1 mL BSTFA and 0.5 ML pyridine on a hot block set @ 80° C. for 1 hour. Following silylation the reagents were removed under nitrogen and the recovered material redissolved in 5 mL toluene. 100 µL was transferred to an auto vial and 1 mL GC-MS grade toluene added for GC-MS analysis.

GC-MS analysis was carried out using a Hewlett Packard 5890 GC (with a 6890 autosampler) coupled to a Quadropole 5972A MSD. The GC was equipped with a 30 m×0.25 mm i.d (0.25 um film thickness) HP5-MS column. The column oven was temperature programmed from 100° C. to 320° C. @ 10° C./min, then held at 320° C. for 8 mins. The detector temperature was set at 320° C. and injector temperature 300° C. The helium carrier gas was set at 0.6 mL/min. The mass range collected was 70–700 daltons using an electron multiplier voltage of 2247 V. 1.0 µL (splitless injection) injection volumes were used.

Further analysis of sub-fraction B of fraction by GCMS demonstrated the presence of the two main components of interest. These components were further isolated using silica chromatography, analysed by 1H and C13 NMR and evaluated in the PPARgamma reporter gene assay (see table 8). One of these components (commipheric acid) was able to activate PPARgamma (see table 8). Two further molecules (commipherol and myrrhanol A—isolated from subfraction C) with a similar structure to commipheric acid were also found to activate PPARgamma to a lesser degree.

GC-MS analysis of the acidic fraction showed that the major component (75% by area) was 13-(decahydro-2-hydroxy-2,5,5,8a-tetramethyl-6-oxo-1-naphthalenyl)-2,6,10-trimethyl-2,6,10-tridecatrienoic acid.

Effect of Purified Components of Guggulipid on Reporter Gene Activity

TABLE 8

| Guggulipid extract | Reporter gene activity* (Fold-induction relative to the vehicle) | | | | | |
|---|---|---|---|---|---|---|
| | Commipheric acid | | Commipherol | | Myrrhanol A | |
| (µg/ml) | Mean | St err | Mean | St err | Mean | St err |
| vehicle | 1 | 0.26 | 1 | 0.32 | 1 | 0.09 |
| 1.25 | 2.56 | 0.51 | 3.41 | 0.19 | 1.14 | 0.38 |

TABLE 8-continued

| Guggulipid extract | Reporter gene activity* (Fold-induction relative to the vehicle) | | | | | |
|---|---|---|---|---|---|---|
| | Commipheric acid | | Commipherol | | Myrrhanol A | |
| (µg/ml) | Mean | St err | Mean | St err | Mean | St err |
| 2.5 | 3.40 | 0.96 | 4.97 | 2.09 | 1.74 | 0.46 |
| 5 | 8.01 | 0.60 | — | — | 3.87 | 1.2 |

(*Reporter gene expression is controlled by PPARgamma and therefore reflects the level of PPARgamma activation)

Analysis of the purified compounds indicates that commipheric acid and components of guggulipid with similar structure such as commipherol and myrrhanol are able to activate PPARgamma. As activation of PPARgamma has positive effects on insulin sensitivity these molecules, particularly commipheric acid and commipherol, are likely to mediate the effects of guggulipid on insulin resistance.

Specific PPARgamma activating compounds present in guggulipid therefore include:

(i) 13-(decahydro-2-hydroxy-2,5,5,8a-tetramethyl-6-oxo-1-naphthalenyl)-2,6,10-trimethyl-, [1R-[1α(2E,6E,10E),2β,4aβ,8aα]]-2,6,10-tridecatrienoic acid (termed commipheric acid)

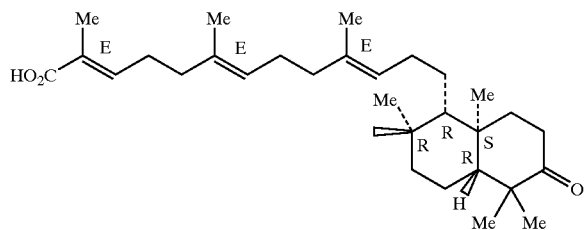

(ii) Octahydro-6-hydroxy-5-(13-hydroxy-4,8,12-trimethyl-3,7,11-tridecatrienyl)-1,1,4a,6-tetramethyl-, [4aS-[4aα,5α(3E,7E,11E),6β,8aβ]]-2(1H)-naphthalenone (also termed commipherol and myrrhanone A)

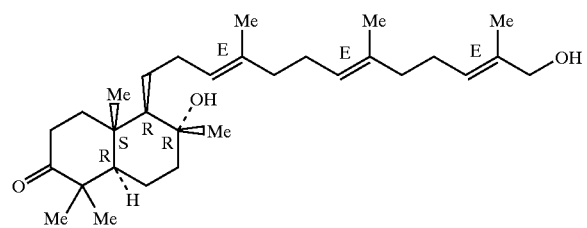

(iii) Decahydro-5-[(3E,7E,11E)-13-hydroxy-4,8,12-trimethyl-3,7,11-tridecatrienyl]-1,1,4a,6-tetramethyl-, (2S,4aS,5R,6R,8aS)-2,6-naphthalenediol (termed myrrhanol A)

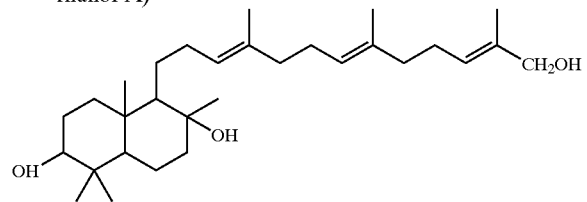

EXAMPLE 2

The Enrichment of Commipheric Acid Using Aminopropyl Solid Phase Extraction Chromatography The acidic components from guggul lipid were isolated by SPE using Varian Mega Bond Elut (2 g) aminopropyl columns. A 2 g aminiopropyl SPE column (Varian mega bond elut) was placed on a vacuum manifold and washed twice with 8 mL of hexane. Approx. 200 mg (weight accurately recorded) guggul lipid (gukkaselect, ex Indena, Milan) was dissolved in 2.0 mL chloroform and applied to the column under gravity. The column was eluted with 18 mL chloroform/2-propanol (2:1) to recover neutral lipids. The column was then eluted with 18 mL 2% acetic acid in diethyl ether to recover the acidic components. The solvent was removed from the recovered fractions under nitrogen on a hot block set at 80° C.

The acidic fraction was analysed using GC-MS analysis and the major component (75% by area) was 13-(decahydro-2-hydroxy-2,5,5,8a-tetramethyl-6-oxo-1-naphthalenyl)-2,6,10-trimethyl-2,6,10-tridecatrienoic acid.

EXAMPLE 3

Comparison of the Effect of Guggulipid Extract and the Guggulsterones on Activation of PPARgamma As illustrated in example 1 guggulipid extract and its constituents commipheric acid, commipherl and myrrhanol are able to promote activation of PPARgamma in the reporter gene assay at levels of 5 µg/ml or less. Using the same reporter gene methodology that is described in example 1 we have tested the ability of two other known constituents of guggulipid (Z- and E-guggulsterones) to determine whether they too can activate PPARgamma.

TABLE 9

Effect of guggulsterones on PPARgamma-mediated reporter gene activity.

| Ligand tested (5 µg/ml) | Reporter gene activity* (Fold-induction relative to the vehicle) | |
| --- | --- | --- |
|  | Mean | St Err |
| Vehicle | 1.0 | 0.28 |
| Guggulipid extract | 6.5 | 0.39 |
| Z-guggulsterone | 0.5 | 0.09 |
| E-guggulsterone | 0.4 | 0.19 |

*Reporter gene expression is controlled by PPARgamma and therefore reflects the level of PPARgamma activiation The data shows that unlike the guggulipid extract neither the E- nor the Z-form of guggulsterone can activate PPAR-gamma. Hence the ability of guggulipid extract to activate PPARgamma and confer anti-insulin resistance properties is due to molecules other than the guggulsterones.

EXAMPLE 4

The Effect of Guggulipid on Adipocyte Differentiation Adipocyte Differentiation Assay 3T3L1 cells (ATCC CL-173) were seeded into the wells of a 24-well plate at a density of $0.375 \times 10^5$ cells/well. The cells were grown in DMEM supplemented with 10% FCS, 2 mM L-glutamine, 100 iu/ml penicillin and 100 µg/ml streptomycin until 2 days post-confluence (day 0). Cells were then incubated for 8–10 days in growth medium supplemented with 5 µg/ml insulin and either guggulipid (Gukkaselect obtained from Indena)or vehicle alone (0.1% ethanol). The medium was changed every 2–3 days. The degree of adipocyte differentiation was assessed qualitatively by oil red O staining. Cells were washed 3× with PBS and then fixed for 15 minutes at room temperature in 10% formalin. After fixation cells were washed 1× in PBS and then stained for 15 minutes in oil red O (prepared in saturated ethanol). After staining the cells were washed several times with sterile water and then viewed under the microscope.

Figure 1:
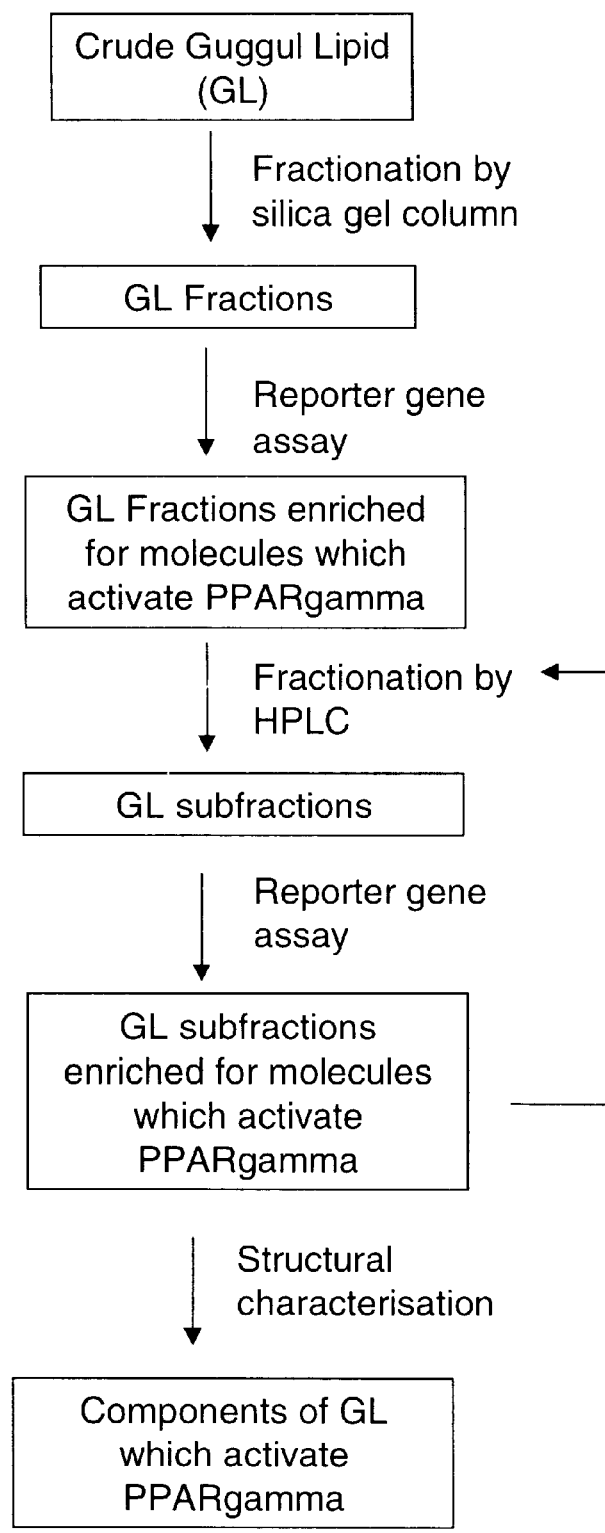
FIG. 1: provides a schematic representation of a process by which PPARgamma activating molecules may be obtained from a guggulipid extract.
Figure 2:
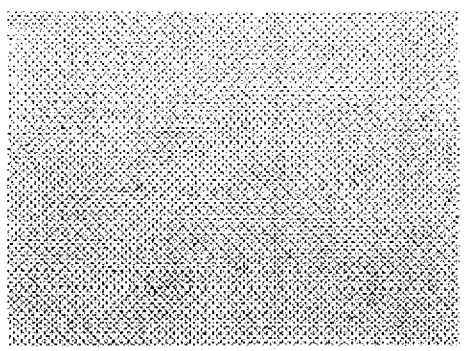
FIG. 2: is a photographic illustration of the finding that guggulipid extract stimulates adipocyte differentiation.
Figure 2:
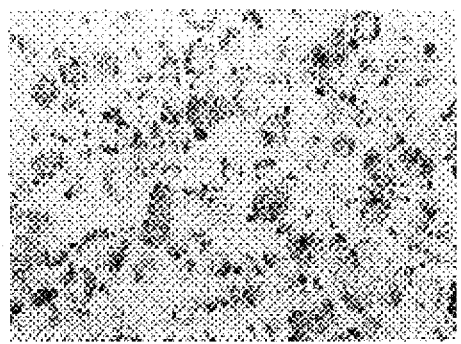

A classical feature of a PPARgamma agonist is to promote adipocyte differentiation. FIG. 2 shows that guggulipid in keeping with its role to activate PPARgamma also promotes adipocyte differentiation. Differentiated cells are denoted by a high degree of oil red O staining. Oil red O specifically stains lipid droplets. These are only present in mature adipocytes.

EXAMPLE 5

Glucose Uptake Assay in Human Skeletal Muscles

Human skeletal muscle cells (SMCs) were obtained from TCS 2000 Ltd. Cells were seeded into 12-well plates at a density of $3 \times 10^4$ cells/well and then grown and differentiated as instructed by TCS. Differentiated human SMCs were incubated, for 32 hours at 37° C./5% $CO_2$, in differentiation media (supplied by TCS) supplemented with an appropriate amount of agent or vehicle. Media was then changed to serum free media (MEM-alpha media, 2 mM glutamine, 100 iu/ml penicillin and 100 µg/ml streptomycin), supplemented as before, and the cells incubated for a further 16 hours.

Cells were then washed 3× with Krebs Ringer Phosphate (KRP) buffer [136 mM NaCl, 4.7 mM KCl, 1.25 mM $CaCl_2$, 1.25 mM $MgSO_4$, 10 mM sodium phosphate buffer, pH 7.4] and incubated in KRP (0.5 ml/well) for 30 minutes at 37° C./5% $CO_2$. After 30 minutes incubation the glucose uptake assay was initiated by addition of 25 µl KRP containing 5 µCi [$^3$H]2-deoxyglucose and 1 mM deoxyglucose. After 10 minutes the reaction was terminated by washing the cells 3× with ice-cold PBS. Cells were then solublised with 125 µl/well of 1% Triton X-100 for 20 minutes at 37° C. Radioactive incorporation was measured by scintillation counting. 100 µl of each sample was analysed.

Ciglitizone is a member of the thiazolidinedione class of compounds and is a known synthetic activator of PPAR-gamma. Here we show that guggulipid extract promotes glucose uptake in a similar manner to the synthetic PPAR-gamma agonist.

TABLE 10

Effect of guggulipid extract on glucose uptake in skeletal muscle cells.

| | [3H] 2-deoxyglucose uptake (Fold-induction relative to vehicle) | | | |
| --- | --- | --- | --- | --- |
| | Guggul lipid (µg/ml) | | Ciglitizone (µM) | |
| | Mean | St Err | Mean | St Err |
| Vehicle | 1.0 | 0.09 | 1.0 | 0.04 |
| 2.5 | 4.1 | 0.20 | 1.3 | 0.08 |
| 5 | 5.6 | 0.67 | 3.3 | 0.10 |

EXAMPLE 6

In vivo Evaluation of Insulin Sensitivity in the ob/ob Mouse

The animals used for the study were female C57Bl/6 ob/ob mice obtained from Harlan Olac U.K. Animals were housed in plastic cages with bedding under the following conditions:

TABLE 11

| Temperature: | 23° C. ± 1° C. |
|---|---|
| Light: | 12 hours light/12 hours dark, lights on at 7 AM |

They were fed a standard laboratory diet—rat and mouse standard diet (Beekay Feed, B & K Universal Ltd, Hull, UK). Drinking water was provided ad libitum.

The mice were allocated to 2 treatment groups; each housed in a separate cage. Initial bodyweights were matched so that all treatments started with mice of similar mean bodyweight. Six days prior to commencement of the study the mice were allocated to individual cages and were provided with food and water ad libitum for acclimatisation. The mice were then maintained on either a powdered standard laboratory diet (control group) or diet containing the guggulipid extract dietary supplement throughout the experiment. Food and water intakes were monitored daily. After 2 weeks of treatment the mice were fasted for 5 hours, oral glucose-tolerances measured, and blood samples taken for analysis of insulin. After 3 weeks of treatment blood was taken when animals were feeding ad libitum for analysis of insulin.

To prepare the dietary supplement guggulipid extract was dissolved in warm ethanol before mixing with the Chow Diet alone. It was then spread thinly over a flat surface and blow-dried at room temperature overnight to remove any traces of ethanol.

Effect of Guggulipid Extract on Glucose Tolerance

Oral glucose tolerance was measured after a two week treatment period. Animals were fasted for 5 hours prior to the start of the glucose tolerance test. Animals were treated with glucose diluted in water at a rate of 3 g/kg P.O. (3 g/10 ml). Blood samples were taken at 0, 30, 60 90 120 and 180 minutes following glucose administration.

For measurement of blood glucose levels, a 20 $\mu$l sample of blood was taken from the tail vein. Glucose concentrations were determined by mixing blood samples with 0.38 ml of haemolysis reagent. Duplicate 20 $\mu$l aliquots of this mixture were taken for each individual sample and placed in a 98 well assay plate. To each well 180 $\mu$l aliquots of Trinders glucose reagent (Sigma Enzymatic (Trinder) calorimetric method. Cat. No. 315-100.) were added. The samples were mixed and then left for approximately 30 minutes. Samples were then analysed automatically using a SpectraMax 250 and SoftMax Pro software (Molecular Devices Corporation, 1311 Orleans Drive, Sunnyvale, Calif., 94089, USA). The results were converted into glucose concentration values using Prism software, version 3.0 (GraphPad Software Inc, San Diego, Calif., USA)

TABLE 12

A Mixed Model was fitted to the data with autoregressive repeated measures. Significance, $p < 0.05$, is indicated*.

| | Blood glucose (mMol/L) | |
|---|---|---|
| Time (in minutes) | Control | Guggulipid extract |
| 0 | 9.69 ± 0.46 | 8.64 ± 0.85 |
| 30 | 18.72 ± 0.45 | 9.82 ± 0.66* |

TABLE 12-continued

A Mixed Model was fitted to the data with autoregressive repeated measures. Significance, $p < 0.05$, is indicated*.

| | Blood glucose (mMol/L) | |
|---|---|---|
| Time (in minutes) | Control | Guggulipid extract |
| 60 | 11.37 ± 0.61 | 7.98 ± 0.0.48* |
| 90 | 11.50 ± 0.72 | 8.06 ± 0.49* |
| 120 | 10.95 ± 0.70 | 8.81 ± 0.56* |
| 180 | 8.43 ± 0.27 | 8.06 ± 0.22 |

Figure 3:
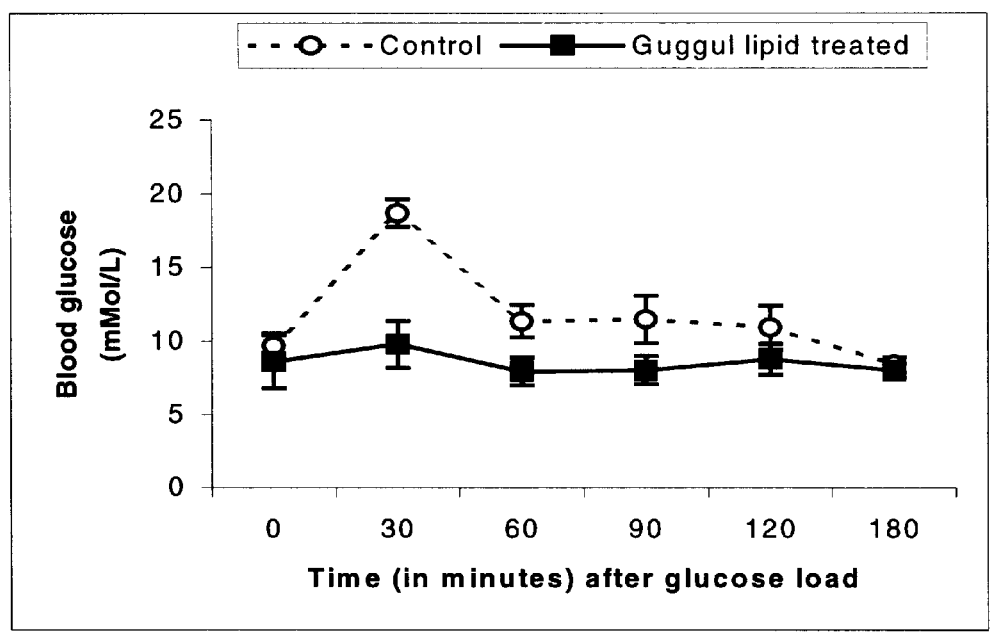
FIG. 3: illustrates that guggulipid treated animals show improved glucose tolerance, wherein after a glucose challenge the blood glucose levels of the guggulipid treated animals normalise more rapidly than control animals.

After 2 weeks of dietary supplementation the animals treated with guggulipid extract showed improved glucose tolerance compared to the control group. After a glucose challenge the blood glucose levels of guggulipid extract treated animals normalised more rapidly (60 minutes as oppose to 180 minutes) than control animals (FIG. 3). The ability of treated animals to respond better to a glucose challenge indicates that dietary supplementation with guggulipid extract reduces the degree of whole body insulin resistance.

Effect of Guggulipid Extract on Plasma Insulin Levels

Blood samples (150 $\mu$l) for plasma insulin analysis were taken after 15 days of treatment when the animals had been fasted for 5 hours, and after 22 days of treatment when the animals were feeding ad libitum.

Blood was collected in heparin coated microvettes (Sarstedt microvette CB 300, ref. 16.443, Aktiengsellschaft & Co. D-51588 Nümbrecht, Germany) and stored on ice, before centrifugation at ~5000×G for 5 minutes. The resulting plasma was stored frozen at −80° C. until required. Plasma insulin was measured using 5 $\mu$l of plasma and compared to a rat insulin standard using a 96 well microassay plate (Crystal Chem. Inc. Catalog #: INSKR020 96 assys).

TABLE 13

**$p < 0.001$, *$p < 0.05$ (paired T-Test)

| | Fasted plasma insulin ($\mu$g/ml) | |
|---|---|---|
| | Control | Guggulipid ex. treated |
| 15 d/Fasted 5 h | 4.81 ± 0.58 | 2.38 ± 0.55** |
| 22 d/Fed ad libitum | 28.89 ± 11.92 | 9.37 ± 6.02* |

A mixed model was fit to the data with unstructured repeated measures.

After 2 weeks of dietary supplementation the animals treated with guggulipid extract showed significantly lower fasted plasma insulin levels than controls. As a lower level of insulin is required by guggulipid extract treated animals to maintain glycaemic control this indicates that the tissue sensitivity to insulin in these animals has been enhanced. These data indicate that dietary supplementation with guggulipid extract reduces insulin resistance and supports the findings from the oral glucose tolerance test.

EXAMPLE 7

In vivo Evaluation in a Genetic Model of Insulin Resistance of an Extract of Guggulipid With High Levels of Commipheric Acid As indicated in example 1 the molecule commipheric acid has been identified as the component of guggulipid which activates PPARgamma. To confirm the activity of commipheric acid in vivo a 2 week dietary supplementation study in female C57Bl/6 ob/ob mice was performed. The study was conducted as described in example 4. The animals were separated into 3 groups (6 animals per group) and fed either a control diet, a diet supplemented with standard guggulipid (Gukkaselect, Indena) at 2%(wt/wt) or a diet supplemented with Enriched GL-1 at 0.7% (wt/wt). Enriched GL-1 is an extract of guggulipid which contains 27.5% commipheric acid (as defined by GC-MS analysis). Standard guggulipid (Gukkaselect, Indena) contains 9.5% commipheric acid (as defined by GC-MS analysis).

Effect on Oral Glucose Tolerance

TABLE 14

| Time (in minutes) | Blood glucose (mMol/L ± SEM) | | |
|---|---|---|---|
| | Control | Guggulipid (2% of diet) | Enriched GL-1 (0.7% of diet) |
| 0 | 7.33 ± 0.24 | 6.26 ± 0.19* | 7.26 ± 0.26 |
| 30 | 16.75 ± 0.72 | 10.52 ± 0.52* | 11.68 ± 0.70* |
| 60 | 11.39 ± 1.40 | 6.33 ± 0.30* | 7.79 ± 0.0.26* |
| 90 | 9.97 ± 0.56 | 6.41 ± 0.13* | 7.52 ± 0.0.33* |
| 120 | 9.66 ± 0.63 | 7.28 ± 0.15* | 7.55 ± 0.0.15* |

A mixed model with unstructured repeated measures was fitted to the data. Significance, $p < 0.05$, indicated as*.

After 2 weeks of dietary supplementation the animals treated with Enriched GL-1 showed a significant improvement in glucose tolerance relative to controls. After a glucose challenge the blood glucose levels of Enriched GL-1 treated animals normalised more rapidly (60 minutes as oppose to more than 120 minutes) than those of control animals. The ability of treated animals to respond better to a glucose challenge indicates that dietary supplementation with Enriched GL-1 is able to reduce the degree of whole body insulin resistance. Furthermore, when compared to standard guggulipid Enriched GL-1 was more active as it provided similar benefits at a lower concentration (0.7% of diet versus 2% of diet). These data support the idea that the molecule commipheric acid is capable of reducing insulin resistance. In addition, they illustrate that enrichment for this molecule can yield extracts with increased potency. The increased potency of such extracts is particularly advantageous in the context of a functional food application as supplementation at a lower level is less likely to have an impact on taste and texture.

Effect on Fasted Plasma Insulin

TABLE 15

| Fasted plasma insulin (µg/ml ± SEM) | | |
|---|---|---|
| Control | Guggulipid (2% of diet) | Enriched GL-1 (0.7% of diet) |
| 1.79 ± 0.44 | 0.85 ± 0.09* | 0.96 ± 0.10* |

One-way analysis of variance was employed to compare the three treatment groups. Significance, $p < 0.05$, is indicated*.

After 2 weeks of dietary supplementation the animals treated with Enriched GL-1 showed significantly lower fasted plasma insulin levels than controls. A reduction in the requirement of insulin to maintain glycaemic control indicates that whole body insulin sensitivity has improved. Furthermore, when compared to standard guggulipid the Enriched GL-1 was more active as it provided similar benefits when used at a lower concentration (0.7% of diet compared to 2% of diet). These data provide further evidence that commipheric acid is the component of guggulipid which is active in reducing insulin resistance.

Effect on Water Consumption

Water consumption for each treatment group was measured each day for the duration of the study.

TABLE 16

| Water consumption (ml/mouse/day ± SEM) | | |
|---|---|---|
| Control | Guggulipid | Enriched GL-1 |
| 4.34 ± 0.08 | 2.20 ± 0.08 | 3.83 ± 0.06 |

Surprisingly, animals treated with guggulipid showed a marked decrease in water consumption compared to control animals. A reduction in water consumption may be undesirable as it could lead to a state of dehydration. In contrast, treatment with Enriched GL-1 had a lower effect on water consumption. This illustrates that the process of enriching for commipheric acid is able to ameliorate the effect of guggulipid on water consumption. Hence an extract of guggulipid which has been enriched for commipheric acid is advantageous over standard guggulipid as it is less likely to lead to dehydration problems.

EXAMPLE 8

In vivo Analysis in a Genetic Model of Insulin Resistance of a Guggulipid Extract With High Levels of Commipheric Acid and Commipherol As indicated in example 1 both commipheric acid and commipherol were both shown to activate PPARgamma. To analyse the activity of a mix of these components in vivo a 2 week dietary supplementation study in female C57Bl/6 ob/ob mice was performed. The study was conducted as described in example 4. The animals were separated into 3 groups (6 animals per group) and fed either a control diet, a diet supplemented with standard guggulipid (Gukkaselect, Indena) at 2%(wt/wt) or a diet supplemented with Enriched GL-2 at 1% (wt/wt). Enriched GL-2 is an extract of guggulipid which contains a mix of commipheric acid and commipherol at a level of 32%(as defined by GC-MS analysis). Standard guggulipid (Gukkaselect, Indena) contains a mix of commipheric acid and commipheral at a level of 17.5%(as defined by GC-MS analysis).

Effect on Oral Glucose Tolerance

TABLE 17

| Time (in minutes) | Blood glucose (mMol/L ± SEM) | | |
|---|---|---|---|
| | Control | Guggulipid (2% of diet) | Enriched GL-2 (1% of diet) |
| 0 | 7.33 ± 0.24 | 6.26 ± 0.19* | 7.05 ± 0.45 |
| 30 | 16.75 ± 0.72 | 10.52 ± 0.52* | 14.11 ± 0.90 |
| 60 | 11.39 ± 1.40 | 6.33 ± 0.30* | 7.86 ± 0.58* |
| 90 | 9.97 ± 0.56 | 6.41 ± 0.13* | 7.93 ± 0.47* |
| 120 | 9.66 ± 0.63 | 7.28 ± 0.15* | 7.20 ± 0.36* |

A mixed model with unstructured repeated measures was fitted to the data. Significance, $p < 0.05$, is indicated*.

After 2 weeks of dietary supplementation the animals treated with Enriched GL-2 showed a significant improvement in glucose tolerance relative to controls. After a glucose challenge the blood glucose levels of Enriched GL-2 treated animals normalised more rapidly (60 minutes as oppose to more than 120 minutes) than those of control animals. The ability of treated animals to respond better to a glucose challenge indicates that dietary supplementation with Enriched GL-2 is able to reduce the degree of whole body insulin resistance. Furthermore, when compared to standard guggulipid Enriched GL-2 was more active as it provided similar benefits at a lower concentration (1% of diet versus 2% of diet). These data support the idea that extracts enriched for a mix of commipheric acid and commipherol are capable of reducing insulin resistance and that the higher the level of the commipheric acid/commipherol mix then the greater the effect.

Effect on Fasted Plasma Insulin

TABLE 18

| | Fasted plasma insulin (µg/ml ± SEM) | |
|---|---|---|
| Control | Guggulipid (2% of diet) | Enriched GL-2 (1% of diet) |
| 1.79 ± 0.44 | 0.85 ± 0.09* | 0.86 ± 0.08* |

One-way analysis of variance was employed to compare the three treatment groups. Significance, $p < 0.05$, is indicated*.

After 2 weeks of dietary supplementation the animals treated with Enriched GL-2 showed significantly lower fasted plasma insulin levels than controls. A reduction in the requirement of insulin to maintain glycaemic control indicates that whole body insulin sensitivity has improved. Furthermore, when compared to standard guggulipid the Enriched GL-2 was more active as it provided similar benefits when used at a lower concentration (1% of diet compared to 2% of diet). These data provide further evidence that a combination of commipheric acid and commipherol can have beneficial effects on insulin resistance and the greater their level the greater the effect.

EXAMPLE 9

Production of Food Product With Commipheric Acid Provided in a Fat Phase

The production of a margarine containing guggul extracts is detailed below. Guggul extracts enriched in commipheric acid were prepared using alkali (aq) neutralisation. 2 g of guggul lipid in 20 mL ether, was shaken with 20 mL of 1% sodium carbonate (aq). Following the addition of brine, the mixture separated into three distinct phases. The middle layer was collected, and washed with ether. The washed middle layer was acidified (dilute HCl) and the product extracted with ether and dried. This product contained 34% commipheric acid by GC/MS. This was enriched to 50% by silica treatment.

| Margarine formulation | % |
|---|---|
| Fat Blend | 83.00 |
| Lecithin | 0.20 |

| Margarine formulation | % |
|---|---|
| Monoglyceride | 0.10 |
| Skimmed milk powder | 0.40 |
| Potassium Sorbate | 0.05 |
| Citric acid to pH 4.7 | |
| Water to 100% | |

Fat Blend=13 in ES/83.5 Palm Oleine/3.5 enriched commipheric acid. (in ES=interesterified; palm oil-58/palm kernel-olein 41 (1:1) ratio)

| | Processing | | |
|---|---|---|---|
| Premix | A unit | C unit | A unit |
| Jacket Temp (° C.) 60 | 6.9 | 16.1 | 9.8 |
| Temp out (° C.) | 13.7 | 17.2 | 13.3 |
| Stirrer Speed (rpm) | 850 | 400 | 600 |

A batch size of 2 kg was used with a throughput of 35 g/min. The fat blend was held at 60° C. prior to formulation. The margarine is produced on a standard microvotator line using the conditions as stated above.

EXAMPLE 10

Emulsions of Guggulipid Extract and Commipheric Acid (i) emulsification of guggul and enriched commipheric acid with Gum arabic:

Gum arabic (10%) was mixed with water (Ph eur Acacia gum ex Fluka) in a large glass vessel and heated to >70° C. with stirring. 14% of guggul or enriched commipheric acid (70% commipheric acid) was added and stirred vigorously, heating to 90–95° C. for approx. 10–20 minutes. The mixture was homogenised using an ultra turrax mixer (whose head had been pre-heated) at high speed for 5 minutes. A white stable emulsion was produced in each case.

(ii) emulsification of Guggul and enriched commipheric acid with buffered sodium caseinate:

A 0.1M solution of sodium dihydrogen phosphate containing 0.88% sodium chloride was produced. The pH was adjusted to 7 by the addition of dilute sodium hydroxide. 3% sodium casienate was added to the buffer and the solution was mixed vigorously with heating 70° C. 14% of Guggul or enriched guggul (70% commipheric acid) were added. After mixing for approx. 10–20 minutes at 90–95° C. the stirrer bar was removed and replaced by an ultra turrax mixer (preheated head) and homogenised for ~5 minutes at high speed. A stable emulsion was produced. Guggul emulsions containing 20%, 30% and 36% guggul were also made using 3% sodium caseinate in water (no salt or buffer) according to the methods detailed above.

What is claimed is:

1. A food composition for the treatment of insulin resistance in humans comprising a member of the group consisting of edible spreads, mayonnaise, dressing, ice cream, dairy and non-dairy creams, confections, bakery products, soups, beverages, jam, cakes, chocolate, dietary supplements, sauces and specialty foods for type-2 diabetics and an effective amount of a compound according to the formula:

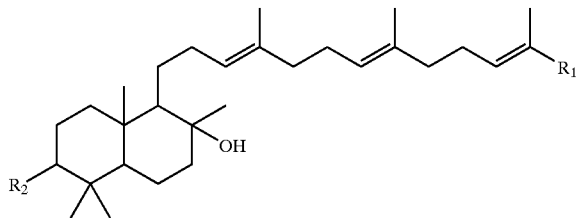

wherein, $R_1$ is selected from the group consisting of COOH, $CH_2OH$ salts and/or esters thereof and $CH_3$; and $R_2$ is selected from the group consisting of OH, O and esters thereof;

wherein said compound is contained within a continuous or discontinuous fat phase.

2. A food composition according to claim 1, wherein said compound is contained within a continuous or discontinuous aqueous phase.

3. A food composition according to claim 1 wherein said compound is present in an amount of at least 0.01% by weight.

4. A food composition according to claim 1 wherein said compound is present in an amount of at least 3% by weight of said composition.

5. A food composition according to claim 1 for use in the treatment of a disease selected from the group consisting of polycystic ovary syndrome, type-2 diabetes, gestational diabetes, syndrome X, hypertension, psoriasis and stroke.

6. A food composition according to claim 1 for use in the treatment of one or more symptoms of insulin resistance selected from the group consisting of reduced energy levels, reduced cognitive performance, tiredness and mood swings.

* * * * *